US006229026B1

(12) United States Patent
Petersen

(10) Patent No.: US 6,229,026 B1
(45) Date of Patent: May 8, 2001

(54) METHOD FOR THE PREPARATION OF CITALOPRAM

(75) Inventor: Hans Petersen, Vanløse (DK)

(73) Assignee: H. Lundbeck, A/S, Copenhagen-Valby (DK)

( * ) Notice: Subject to any disclaimer, the term of this patent is extended or adjusted under 35 U.S.C. 154(b) by 0 days.

(21) Appl. No.: 09/479,832

(22) Filed: Jan. 7, 2000

Related U.S. Application Data

(63) Continuation of application No. PCT/DK98/00081, filed on Jul. 8, 1998.
(60) Provisional application No. 60/052,788, filed on Jul. 8, 1997.

(30) Foreign Application Priority Data

Jul. 8, 1997 (DK) .................................................. 0826/97

(51) Int. Cl.[7] ..................... C07D 307/83; C07C 233/64; C07C 69/76
(52) U.S. Cl. ........................... 549/467; 514/456; 560/62; 564/171
(58) Field of Search ............................. 560/62; 564/171; 514/456; 549/467

(56) References Cited

U.S. PATENT DOCUMENTS 3,467,675     9/1969   Petersen et al. .................. 260/346.2

FOREIGN PATENT DOCUMENTS

| 26 57 013 A1 | 7/1977 | (DE) | ............................. C07D/307/87 |
| 0 171 943 A1 | 2/1986 | (EP) | ............................. C07C/121/80 |
| WO 92/22554 | 12/1992 | (WO) | ........................ C07D/491/107 |

OTHER PUBLICATIONS

Bigler AJ. et al "Quantitative structure–activity relationships in a series of selective 5–HT uptake inhibitiors" CA 87;161413, 1977.*

Moltzen, Ejner K. et al., "σ Ligands with Subnanomolar Affinity and Preference for the σ2 Binding Site 2. Spiro–Joined Benzofuran, Isobenzofuran, and Benzopyran Piperidines," *J. Med. Chem.* 38: 2009–2017 (1995).

Bigler, Allan J. et al., "Quantitative structure–activity relationships in a series of selective 5–HT uptake inhibitors," *Eur. J. Med. Chem.—Chemica Therapeutica* 12, 3: 289–295 (May–Jun. 1977).

* cited by examiner

*Primary Examiner*—Amelia Owens
(74) *Attorney, Agent, or Firm*—Darby & Darby

(57) ABSTRACT

A method for the preparation of citalopram comprising the steps of reacting a compound of Formula (IV) wherein $R^1$ is $C_{1-6}$ alkyl and X is O or NH, successively with a Grignard reagent of 4-halogen-fluorophenyl and a Grignard reagent of 3-halogen-N,N-dimethylpropylamine, respectively, effecting ring-closure of the resulting compound of Formula (V) wherein $R^1$ and X are as defined above, and converting the resulting 1,3-dihydroisobenzofuran compound to the corresponding 5-cyano derivative, i.e. citalopram.

27 Claims, No Drawings

METHOD FOR THE PREPARATION OF CITALOPRAM

This application claims benefit of provisional application No. 06/052,788 filed Jul. 8, 1997.

This is a continuation of International Application No. PCT/DK98/00081, filed Jul. 8, 1998, the entire disclosure of which is hereby incorporated by reference.

The present invention relates to a method for the preparation of the well known antidepressant drug citalopram, 1-[3-(dimethylamino)propyl]-1-(4-fluorophenyl)-1,3-dihydro-5-isobenzofurancarbonitrile and intermediates used in the method.

BACKGROUND OF THE INVENTION

Citalopram is a well known antidepressant drug that has now been on the marked for some years and has the following structure:

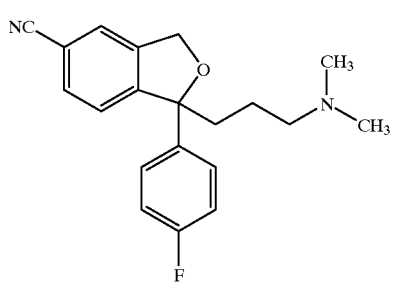

Formula I

It is a selective, centrally active serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75 , 478–486. The compound has further been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

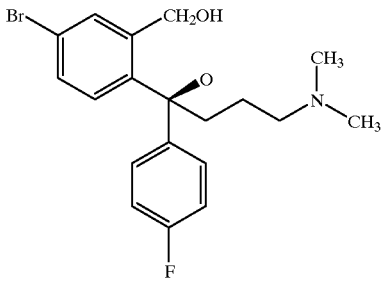

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram is described in U.S. Pat. No. 4,650,884 according to which an intermediate of the formula

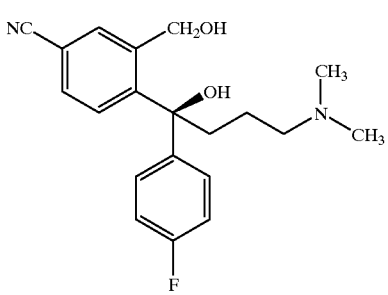

Formula III is subjected to a ring-closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Finally, methods of preparing the individual enantiomers of citalopram are disclosed in U.S. Pat. No. 4,943,590 from which it also appears that the ring closure of the intermediate of Formula III may be carried out in basic conditions.

It has now surprisingly been found that citalopram may be manufactured by a favourable and safe procedure using convenient starting materials.

SUMMARY OF THE INVENTION

Accordingly, the present invention relates to a novel method for the preparation of citalopram comprising the steps of reacting a compound of Formula IV

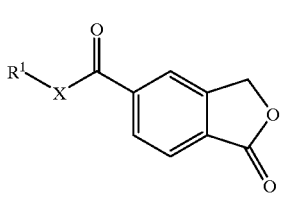

Formula IV wherein $R^1$ is $C_{1-6}$ alkyl and X is O or NH, successively with a Grignard reagent of 4-halogen-fluorophenyl, thereby obtaining a compound of Formula IVa Formula IVa

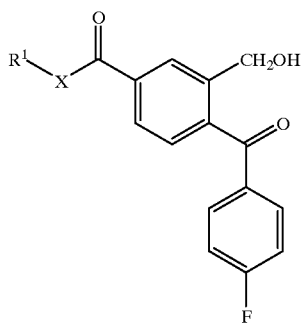

wherein $R^1$ and X are as defined above, and a Grignard reagent of 3-halogen-N,N-dimethylpropylamine, effecting ring closure of the resulting compound of Formula V Formula V

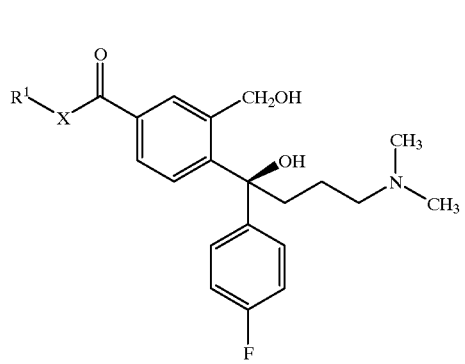

wherein $R^1$ and X are as defined above, and converting the resulting compound of Formula VI Formula VI

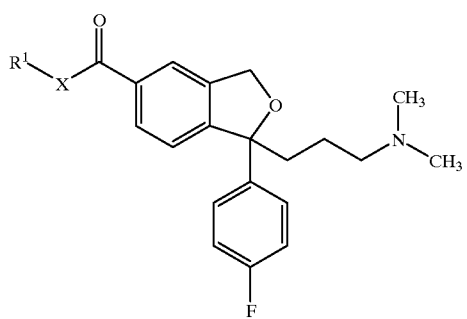

where $R^1$ and X are as defined above, to the corresponding 5-cyano derivative, i.e. citalopram, which is isolated as the base or a pharmaceutically acceptable salt thereof In another aspect the present invention provides the novel intermediates of Formulas IVa and V, respectively.

In a further aspect the present invention provides the novel intermediates of Formula VI.

In yet another aspect the present invention relates to an antidepressant pharmaceutical composition comprising citalopram manufactured by the process of the invention.

Throughout the specification and claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Grignard reagents of 4-halogen-fluorophenyl that may be used in the first step are the magnesium halogenides, such as the chloride, bromide or iodide. Preferably the magnesium bromide is used. Grignard reagents of 3-halogen-N,N-dimethylpropylamine that may be used are the magnesium halogenides, such as the chloride, bromide or iodide, preferably the magnesium bromide. The intermediate of Formula IVa may or may not be isolated Preferably the two reactions are performed successively without isolation of the intermediate.

The ring-closure of the compound of Formula V is effected by an acid or via a labile ester with a base. Acidic ring closure is performed by an inorganic acid, such as a sulfuric or phosphoric acid, or an organic acid, such as methylsulfonic, p-toluenesulfonic or trifluoroacetic acid. The basic ringclosure is performed via a labile ester, such as the methane sulfonyl, p-toluene sulfonyl, 10-camphorsulfonyl, trifluoroacetyl or trifluoromethanesulfonyl ester with addition of a base, such as triethyl amine, dimethylaniline, pyridine, etc. The reaction is performed in an inert solvent, preferably with cooling, in particular about 0° C. and is preferably carried out by a one-pot procedure, i.e. with esterification and simultaneous addition of the base.

When X is O, the conversion of the group $R^1$—X—CO— to cyano is preferably performed via the corresponding amide group which is then converted to the cyano group in the same way as compounds of Formula VI wherein X is NH.

The reaction of $R^1$—X—CO— (X=O) to amide is carried out by hydrolysis with an acid or a base and subsequent conversion to acid chloride and amidation by reaction with ammonia or an alkylamine, preferably t-butyl amine. Acid hydrolysis may be performed by use of any suitable acid, such as HBr, HCl, HBr/acetic acid. Basic hydrolysis may be performed with any suitable base, such as $K_2CO_3$, NaOH, KOH, etc. The conversion to amide may also be obtained by reaction of the ester (X=O) with ammonia or an alkylamine under pressure and heating.

The amide is converted to the cyano group by conventional nitril synthesis. So, the resulting amide or the amide of Formula V wherein X is NH is preferably converted to the cyano compound, i.e. citalopram, by reaction with a dehydrating agent, most preferably thionyl chloride, phosphor pentachloride, etc.

Alternatively, an ester, i.e. a compound of Formula VI wherein X is O may be hydrolysed and then reacted with chlorosulfonyl isocyanate in order to form the nitrile.

The process of the invention may be carried out with or without isolation of the intermediates.

The process of the invention may also be used to prepare the active (S)-enantiomer of citalopram. In that case, the compound of formula V is separated into the optically active enantiomers by a procedure analogous to the one described in U.S. Pat. No. 4,943,590 thereby obtaining the (S)-nantiomer of the compound of formula V which is used in the ring closure reaction in step c). Accordingly, the individual enantiomers of the intermediates of formulas V and VI, respectively, are embraced by the formulas.

Other reaction conditions, solvents, etc. are conventional conditions for such reactions and may easily be determined by a person skilled in the art.

The starting materials of formula IV are commercially available or may be prepared from 5-carboxyphtalide by reaction with thionyl chloride and then $C_{1-6}$ alkanol or $C_{1-6}$ alkylamine. 5-carboxyphtalide is commercially available and may be prepared by well known procedures (Tirouflet, J.; Bull.Soc.Sci. Bretagne 26, 1959,35).

In one embodiment of the invention X is O and $R^1$ is ethyl, propyl, or butyl, preferably ethyl, 2-propyl or t-butyl.

In another embodiment of the invention X is NH and $R^1$ is ethyl, propyl, or butyl, preferably ethyl, 2-propyl or t-butyl, most preferably t-butyl.

The compound of general Formula I may be used as the free base or as a pharmacologically acceptable acid addition salt thereof. As acid addition salts such salts formed with organic or inorganic acids may be used. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

EXAMPLES

Example 1

5-tert. Butoxycarbonylphthalid

5-Carboxyphthalid (100 g, 0.56 mole) is suspended in pyridine (1200 mL). p-toluenesulfonyl chloride (211 g, 1.12 mole) is added and the mixture is stirred for 30 minutes at room temperature. Tert.Butanol (54 g, 0.73 mole) is added and the reaction mixture is left at room temperature with efficient stirring for 3 days. The clear solution is poured into ice water and the precipitated crystals are filtered off. The product is recrystallized from 2-propanol (500 mL). Yield: 123 g, 94%. DSC onset: 151.5° C.

Example 2

5-(2-Propyloxycarbonyl)phthalid

Method A): 5-Carboxyphthalid (36 g, 0.2 mole) is suspended in thionylchloride (100 mL). DMF (1.5 mL) is added and the mixture is refluxed for 1 hour. Toluene (200 mL) is added and the solvents are evaporated off in vacuo. 2-Propanol (200 mL) is added and the mixture is refluxed for 30 minutes. After cooling to 0° C. the crystals are filtered off and washed with cold 2-propanol (50 mL). Yield: 38 g, 87%. DSC onset: 144° C.

Method B): 5-Ethoxycarbonylphthalid (52 g, 0.25 mole) is suspended in 2-propanol (1000 mL). Ti(iPro)$_4$ (38 g, 0.14 mole) is added and the mixture is refluxed for 3 hours. The reaction mixture is cooled to 0° C. and the crystals are filtered off and washed with cold 2-propanol (70 mL). Yield: 47 g, 85%. DSC onset 144° C.

Example 3

5-tert.Butylcarbamylphthalid

5-Carboxyphthalid (36 g, 0.2 mole) is suspended in thionylchloride (100 mL). DMF (1.5 mL) is added and the mixture is refluxed for 1 hour. Toluene (200 mL) is added and the solvents are evaporated in vacuo. The residue is dissolved in THF (200 mL) and added to a solution of tert.butylamine (31 g, 0.42 mole) in THF (200 mL) at 5° C. The mixture is allowed to warm to room temperature and stirred overnight. The reaction is then poured into ice water (400 mL) and the precipitated crystals are filtered off. The crystals are washed with water (100 mL). Yield: 41 g, 87%. DSC onset: 189.5° C.

Example 4

Tert.-butyl 1-(3-dimethylaminopropyl)-1-(4-fluorophenyl)-1,3-dihydroisobenzofuran-5-carboxylate, oxalate A solution of 4-fluorophenylmagnesium bromide, prepared from 4-fluorobromobenzene (31.5 g, 0.18 mole) and magnesium turnings (5.1 g, 0.21 mole) in dry THF (150 mL), is added dropwise to a suspension of 5-tert.butoxycarbonylphthalid (35.1 g, 0.15 mole) in dry THF (150 mL). The temperature is kept below 5° C. After the addition is complete, the reaction mixture is stirred for 3 hours at room temperature. A second Grignard solution prepared from 3-dimethylaminopropyl chloride (21.9 g, 0.18 mole) and magnesium turnings (5.1 g, 0.21 mole) in dry THF (150 mL) is added to the reaction mixture. The temperature is kept below 10° C. during the addition. The reaction is left overnight at room temperature with stirring. The reaction mixture is poured into ice water (300 mL) and a saturated solution of ammonium chloride (100 mL). THF is evaporated in vacuo. Ethyl acetate (300 mL) is added and the organic phase is separated and washed with water (2×100 mL) and brine (50 mL). The organic phase is extracted with 2 M HCl (2×100 mL). To the aqueous phase is added 4 M NaOH (100 mL) to give a final pH of 9 or higher. The water layer is extracted with ethyl acetate (400 mL) and the organic phase is washed with water (100 mL), brine (50 mL) and dried with MgSO$_4$ (20 g). To the organic phase is added triethylamine (45.5 g, 0.45 mole) and the solution is cooled to 5° C. Methanesulfonyl chloride (19.5 g, 0.17 mole) in ethyl acetate (100 mL) is added dropwise and after addition the reaction mixture is left for one hour with stirring. The reaction mixture is washed with 0.1 M NaOH (2×100 mL) and the organic phase is dried (MgSO$_4$, 10 g) and the solvent is evaporated in vacuo. The thus obtained material (15 grams of the title compound as its free base) is dissolved in acetone (120 mL) and treated with anhydrous oxalic acid (13.5 g, 0.15 mole) dissolved in acetone (120 mL). The mixture is left at room temperature overnight and the precipitated oxalate is filtered off. Yield: 34 g, 43%. DSC onset 172° C. $^1$H NMR DMSO-d$_6$, 500 MHz): 1.43 (1H, m), 1.47–1.57 (10 H, s+m), 2.21 (2H, t, J=10 Hz), 2.63 (6H, s), 2.97 (2H, t, J=10 Hz), 5.14 (1H, d, J=12.5 Hz), 5.22 (1H, d, J=12.5 Hz), 7.16 (2H, t, J=8.5 Hz), 7.56 (2H, dt, J=1.2 Hz J=8.5 Hz), 7.60 (1H, d, J=8.5 Hz), 7.82 (1H, s), 8.86 (1H, d, J=8.5 Hz).

Anal. calcd. for $C_{26}H_{32}N_1F_1O_7$; C, 63.78: H, 6.60: N, 2.86. Found C, 63.95: H, 6.51: N, 3.14.

In a similar way the following compounds were prepared from S-(2-Propyloxycarbonyl)phthalid and from 5-(ethoxycarbonyl)phthalid, respectively:

2-Propyl 1-(3-dimethylaminopropyl)-1-(4-fluorophenyl)-1,3-dihydroisobenzofuran-5-carboxylate, oxalate Yield 20 g, (42%) from acetone. DSC onset: 79° C. $^1$H NMR (DMSO-d$_6$, 250 MHz): 1.40 (6H, d, J=6.5 Hz), 1.40–1.60 (2 H, m), 2.20 (2H, t, J=10 Hz), 2.63 (6H, s), 2.98 (2H, t, J=10 Hz), 5.12 (1H, heptet, J=6.5 Hz), 5.15 (1H, d, J=12.5 Hz), 5.24 (1H, d, J=12.5 Hz), 7.18 (2H, t, J=8.5 Hz), 7.57 (2H, dt, J=1.2 Hz J=8.5 Hz), 7.63 (1H, d, J=8.5 Hz), 7.88 (1H, s), 8.90 (1H, d, J=8.5 Hz).

Anal. calcd. for $C_{23}H_{28}N_1F_1O_3$, 1.1(COOH)$_2$; C, 62.41: H, 6.27: N, 2.90. Found C, 62.41: H, 6.34: N, 3.21.

Ethyl 1-(3-dimethylaminopropyl)-1-(4-fluorophenyl)-1,3-dihydroisobenzofuran-5-carboxylate, oxalate Yield 14.1 g, (30%) from acetone. DSC onset: 148° C. $^1$H NMR (DMSO-d$_6$, 500 MHz): 1.31 (3H, t, J=7.5 Hz), 1.44 (1H, m), 1.55 (1H, m), 2.22 (2H, t, J=10 Hz), 2.64 (6H, s), 3.00 (2H, t, J=10 Hz), 4.39 (2H, q, J=7.5 Hz), 5.15 (1H, d, J=12.5 Hz), 5.23 (1H, d, J=12.5 Hz), 7.15 (2H, t, J=8.5 Hz), 7.58 (2H, dt, J=1.2 Hz J=8.5 Hz), 7.65 (1H, d, J=8.5 Hz), 7.89 (1H, s), 8.92 (1H, d, J=8.5 Hz).

Anal. calcd. for $C_{26}H_{32}N F_1O_7$, 1.5 H$_2$O; C, 59.00: H, 6.40: N, 2.86. Found C, 58.99: H, 5.93: N, 2.92.

Example 5

5-(tert.Butylcarbamyl)-1-(3-dimethylaminopropyl)-1-(4-fluorophenyl)-1,3-dihydroisobenzofuran, oxalate A solution of 4-fluorophenylmagnesium bromide, prepared from 4-fluorobromobenzene (42 g, 0.24 mole) and magnesium turnings (7 g, 0.29 mole) in dry THF (120 mL), is added dropwise to a suspension of 5-tert.butylcarbamylphthalid (23.3 g, 0.1 mole) in dry THF (120 mL). The temperature is kept below 5° C. After the addition is complete, the reaction mixture is stirred for 3 hours at room temperature. A second Grignard solution prepared from 3-dimethylaminopropyl chloride (14.6 g, 0.12 mole) and magnesium turnings (3.4 g, 0.14 mole) in dry TBF (100 mL) is added to the reaction mixture. The temperature is kept below 10° C. during the addition. The reaction is left overnight at room temperature with stirring. The reaction mixture is poured into ice water (250 mL) and a saturated solution of ammonium chloride (100 mL). THF is evaporated off in vacuo. Ethyl acetate (300 mL) is added and the organic phase is separated and washed with water (2×100 mL) and brine (50 mL). The organic phase is extracted with 2 M HCl (2×100 mL). To the aqueous phase is added 4 M NaOH (100 mL) to give a final pH of 9 or higher. The water layer is extracted with ethyl acetate (400 mL) and the organic phase is washed with water (100 mL), brine (50 mL) and dried with MgSO$_4$ (20 g). To the organic phase is added triethylamine (45.5 g, 0.45 mole) and the solution is cooled to 5° C. Methanesulfonyl chloride (19.5 g, 0.17 mole) in ethyl acetate (100 mL) is added dropwise and after addition the reaction mixture is left for one hour with stirring. The reaction mixture is washed with 0.1 M NaOH (2×100 mL) and the organic phase is dried (MgSO$_4$, 10 g) and the solvent is evaporated in vacuo. The thus obtained material (15 grams of the title compound as its free base) is dissolved in acetone (100 mL) and treated with anhydrous oxalic acid (10 g, 0.11 mole) dissolved in acetone (100 mL). The mixture is left at room temperature with stirring for 3 days and the precipitated oxalate is filtered off. Yield: 7 g, 14%. DSC onset: 167° C. $^1$H NMR (DMSO-d$_6$, 500 MHz): 1.35 (9H, s), 1.37–1.58 (2 H, m+m), 2.21 (2H, t, J=10 Hz), 2.61 (6H, s), 2.96 (2H, t, J=10 Hz), 5.12 (1H, d, J=12.5 Hz), 5.20 (1H, d, J=12.5 Hz), 7.15 (2H, t, J=8.5 Hz), 7.52 (1H, d, J=8.5 Hz), 7.57 (2H, dt, J=1.3 Hz J=8.5 Hz), 7.67–7.75 (3H, s+br s+d, J=8.5 Hz).

Anal. calcd. for $C_{26}H_{32}N_1F_1O_7$; C, 63.91: H, 6.82: N, 5.73. Found C, 63.53: H, 6.82: N, 5.81.

Example 6

1-(3-Dimethylaminopropyl)-1-(4-fluorophenyl)-1,3-dihydroisobenzofuran-5-carbonitrile, oxalate Method A): tert. Butyl 1-(3-dimethylaminopropyl)-1-(4-fluorophenyl)-1,3-dihydroisobenzofuran-5-carboxylate, oxalate (20 g, 0.048 mole) is dissolved in acetic acid (100 mL). HBr (20 mL, 33% in AcOH) is added and left with stirring for 10 min. The solvents are removed in vacuo and the residue is coevaporated with toluene (100 mL). The residue is dissolved in toluene (80 mL) and thionylchloride (80 mL). DMF (1 mL) is added and the mixture is refluxed for 1 hour. The solvents are removed in vacuo and the residue is dissolved in ethyl acetate (100 mL). NH$_4$OH (100 mL, 25% in water) and ice (100 g) is mixed and added and left with good stirring for 30 minutes. The organic phase is washed with water (50 mL) and brine (20 mL) and dried with MgSO$_4$ (10 g). The solvents are removed in vacuo and the residue is dissolved in thionylchloride (40 mL) and refluxed for 2 hours. Toluene (100 mL) is added and the solvents are removed in vacuo. Toluene (100 mL) is added and the organic phase is washed with 2 N NaOH (100 mL) and water (50 mL). The solvents are removed in vacuo. The thus obtained product is purified by flash chromatography which affords the title compound as the free base as an oil. The oxalic acid salt is crystallized from acetone. Yield: 9.0 g (43%). DSC onset 156° C. $^1$H NMR (DMSO-d$_6$, 500 MHz): 1.40 (1H, m), 1.50 (1 H, m), 2.21 (2H, t, J=10 Hz), 2.61 (6H, s), 2.95 (2H, t, J=10 Hz), 5.15 (1H, d, J=12.5 Hz), 5.22 (1H, d, J=12.5 Hz), 7.17 (2H, t, J=8.5 Hz), 7.58 (2H, dt, J=1.2 Hz J=8.5 Hz), 7.63 (1H, d, J=8.5 Hz), 7.80 (1H, d, J=8.5 Hz), 8.82 (1H, s).

Anal. calcd. for $C_{22}H_{23}N_2F_1O_5$; C, 63.75: H, 5.60: N, 6.76. Found C, 63.12: H, 6.59: N, 6.66.

Method B): 5-(tert. Butylcarbamyl)-1-(3-dimethylaminopropyl)-1-(4-fluorophenyl)-1,3-dihydroisobenzofuran, oxalate (1 g, 0.002 mole) is dissolved in thionylchloride (10 mL) and the mixture is refluxed for 2 hours. Toluene (10 mL) is added and the solvents are removed in vacuo. The residue is dissolved in ethyl acetate (15 mL). NH$_4$OH (5 mL, 25% in water) and ice (5 g) is mixed and added and the phases are separated. The organic phase is washed with water (10 mL) and dried with MgSO$_4$. After the solvent is removed in vacuo the title compound is crystallised from acetone. Yield 0.66 g, 78%. DSC onset: 156° C.

What is claimed is:

1. A method for the preparation of citalopram, comprising the steps of reacting a compound of Formula IV

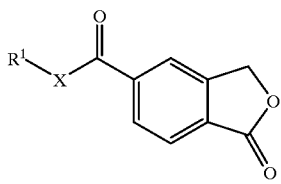

(IV)

wherein R$^1$ is C$_{1-6}$ alkyl and X is O or NH, successively with a Grignard reagent of 4-halogenfluorophenyl, thereby obtaining a compound of Formula IVa

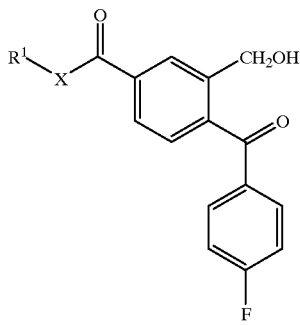

(IVa)

wherein R$^1$ and X are as defined above, and a Grignard reagent of 3-halogen-N,N-dimethyl-propylamine, thereby effecting ring-closure of the resulting compound of Formula V

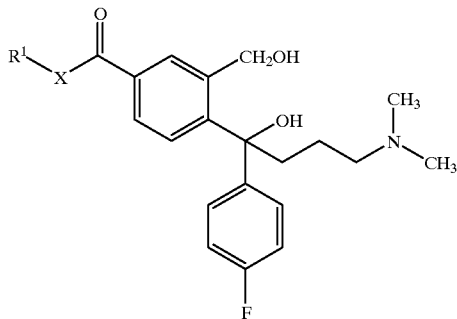

(V)

wherein R$^1$ and X are as defined above, and converting the resulting compound of Formula VI

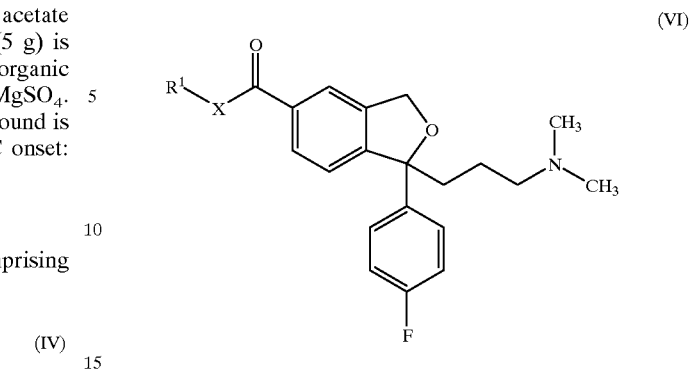

(VI)

wherein R$^1$ and X are as defined above, to the corresponding 5-cyano derivative citalopram, which is isolated as a base or a pharmaceutically acceptable salt thereof.

2. The method of claim 1 wherein X is O.
3. The method of claim 1 wherein X is NH.
4. The method of claim 1 wherein R$^1$ is ethyl, propyl or butyl.
5. The method of claim 4 wherein R$^1$ is ethyl, 2-propyl or t-butyl.
6. The method of claim 1 wherein both said Grignard reagents are magnesium halogenides wherein said halogenides are selected from the group consisting of chloride, bromide or iodide.
7. The method of claim 6 wherein the Grignard reagent of 4-halogen fluorophenyl is the magnesium bromide salt.
8. The method of claim 6 wherein the Grignard reagent of 3-halogen-N,N-dimethylpropylamine is the magnesium chloride salt.
9. The method of claim 1 wherein the ring-closure of the compound of Formula V is effected by acidic ring-closure performed by an inorganic acid or an organic acid.
10. The method of claim 9 wherein said ring-closure is performed by an inorganic acid selected from the group consisting of sulfuric acid or phosphoric acid.
11. The method of claim 9 wherein said ring-closure is performed by an organic acid selected from the group consisting of methylsulfonic acid, p-toluenesulfonic acid or trifluoroacetic acid.
12. The method of claim 1 wherein the ring-closure of the compound of Formula V is a basic ring-closure via a labile ester.
13. The method of claim 12 wherein said basic ring-closure further comprises simultaneous esterification and addition of a base.
14. The method of claim 13 wherein the labile ester is selected from the group consisting of methane sulfonyl, p-toluene sulfonyl, 10-camphorsulfonyl, trifluoroacetyl or trifluoromethanesulfonyl ester, and the base is selected from the group consisting of triethyl amine, dimethylaniline or pyridine.
15. The method of claim 2 wherein X is O and the conversion of the group R$^1$—X—CO— to cyano is performed via the corresponding amide group.
16. The method of claim 14 wherein the reaction of R$^1$—X—CO— to amide is carried out by hydrolysis with an acid or a base, subsequent conversion to acid chloride and amidation by reaction with ammonia or an alkylamine.
17. The method of claim 16 wherein said amidation occurs by reaction with an alkylamine and said alkylamine is t-butyl amine.
18. The method of claim 16 wherein said hydrolysis is performed by use of an acid and said acid is selected from the group consisting of HBr, HCl and HBr/acetic acid.
19. The method of claim 16 wherein said hydrolysis is performed by use of a base selected from the group consisting of K$_2$CO$_3$, NaOH or KOH.

20. The method of claim 16 wherein said reaction of the ester with ammonia or an alkylamine occurs under pressure and heating.

21. The method of claim 15 wherein said amide is converted to the cyano group by reaction with a dehydrating agent.

22. The method of claim 21 wherein said dehydrating agent is selected from the group consisting of thionyl chloride and phosphor pentachloride.

23. A process of claim 1 wherein prior to the ring closure reaction the compound of formula V is separated into optically active enantiomers, thereby obtaining the (S)-enantiomer.

24. An intermediate for preparation of citalopram having Formula IVa

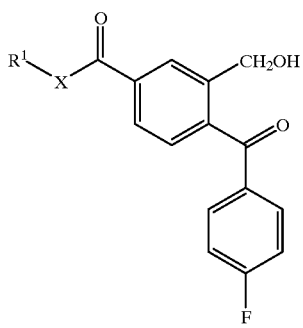

(IVa)

wherein $R^1$ is $C_{1-6}$ alkyl and X is O or NH.

25. An intermediate for preparation of citalopram having Formula V (V)

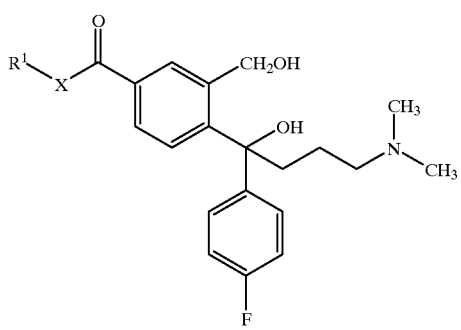

wherein $R^1$ is $C_{1-6}$ alkyl and X is O or NH.

26. An intermediate for preparation of citalopram having Formula VI

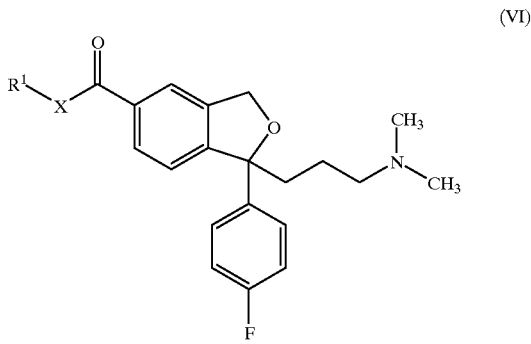

(VI)

wherein $R^1$ is $C_{1-6}$ alkyl and X is O or NH.

27. A method for the preparation of citalopram, or a pharmaceutically acceptable acid addition salt thereof, said method comprising the step of converting a compound of formula VI

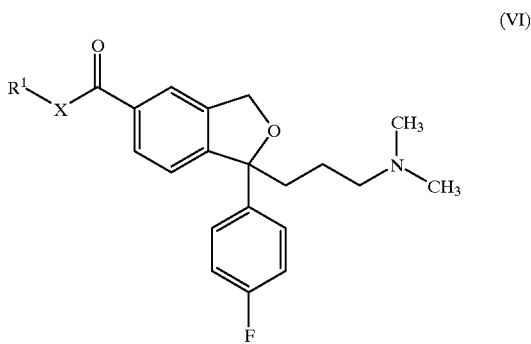

(VI)

wherein $R^1$ is $C_{1-6}$ alkyl and X is O or NH, to the corresponding 5-cyano derivative citalopram.

* * * * *

UNITED STATES PATENT AND TRADEMARK OFFICE
CERTIFICATE OF CORRECTION

PATENT NO.    : 6,229,026 B1                                    Page 1 of 1
DATED         : May 8, 2001
INVENTOR(S)   : Hans Petersen It is certified that error appears in the above-identified patent and that said Letters Patent is hereby corrected as shown below:

<u>Title page,</u>
Item [63], Related U.S. Application Data, change "PCT/DK98/00081, filed on July 8, 1998" to -- PCT/DK98/00081, filed on March 3, 1998 --.

Signed and Sealed this

Twenty-eighth Day of May, 2002

Attest:

JAMES E. ROGAN
*Attesting Officer*        *Director of the United States Patent and Trademark Office*